(12) United States Patent
Hagiwara et al.

(10) Patent No.: US 9,978,122 B2
(45) Date of Patent: May 22, 2018

(54) ELECTRONIC ENDOSCOPE

(71) Applicant: HOYA CORPORATION, Tokyo (JP)

(72) Inventors: Masayuki Hagiwara, Tokyo (JP); Katsuya Tannai, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 280 days.

(21) Appl. No.: 14/807,087

(22) Filed: Jul. 23, 2015

(65) Prior Publication Data

US 2016/0035064 A1 Feb. 4, 2016

(30) Foreign Application Priority Data

Jul. 30, 2014 (JP) ................. 2014-155077

(51) Int. Cl.
*A61B 1/045* (2006.01)
*H04N 19/423* (2014.01)
(Continued)

(52) U.S. Cl.
CPC ........ *G06T 3/4007* (2013.01); *A61B 1/00009* (2013.01); *A61B 1/045* (2013.01);
(Continued)

(58) Field of Classification Search
CPC .. G06T 3/4007; H04N 19/423; H04N 5/2256; H04N 5/23296; H04N 5/2628;
(Continued)

(56) References Cited

U.S. PATENT DOCUMENTS 4,951,125 A  8/1990 Kojima et al.
5,283,651 A  2/1994 Ishizuka
(Continued)

FOREIGN PATENT DOCUMENTS

JP  01-261086 A  10/1989
JP  H01-261086 A  10/1989
(Continued)

OTHER PUBLICATIONS

Search Report issued by E.P.O. patent office in E.P.O. Patent Application No. 15178626.6, dated Nov. 5, 2015.
(Continued)

*Primary Examiner* — William C Vaughn, Jr.
*Assistant Examiner* — Jae N Noh
(74) *Attorney, Agent, or Firm* — Greenblum & Bernstein P.L.C.

(57) ABSTRACT

An electronic endoscope system has an image sensor driver configured to read one line's worth of image-pixel signals in order; at least four line memories configured to store one line's worth of image-pixel signals, respectively; and an interpolation processor that interpolates image-pixel signals of interpolated scanning lines to generate an enlarged image. The interpolation processor generates one line's worth of interpolated image-pixel signals based on image-pixel signals that are stored in the line memories. The image sensor driver reading one line's worth of image-pixel signals intermittently, and the interpolation processor suspends a writing of image-pixel signals that are stored in the line memories in accordance to a suspension of the outputting of the one line's worth of image-pixel signals from the image sensor.

4 Claims, 6 Drawing Sheets

(51) Int. Cl.
*G06T 3/40* (2006.01)
*A61B 1/00* (2006.01)
*A61B 1/05* (2006.01)
*H04N 5/341* (2011.01)
*H04N 5/225* (2006.01)
*H04N 5/372* (2011.01)
*H04N 5/3728* (2011.01)
*H04N 9/04* (2006.01)
*H04N 5/232* (2006.01)
*H04N 5/262* (2006.01)
*H04N 7/01* (2006.01)

(52) U.S. Cl.
CPC ............ *A61B 1/05* (2013.01); *H04N 5/2256* (2013.01); *H04N 5/23296* (2013.01); *H04N 5/2628* (2013.01); *H04N 5/341* (2013.01); *H04N 5/3728* (2013.01); *H04N 5/37213* (2013.01); *H04N 7/012* (2013.01); *H04N 9/045* (2013.01); *H04N 19/423* (2014.11); *H04N 2005/2255* (2013.01)

(58) Field of Classification Search
CPC ...... H04N 5/341; H04N 5/3728; H04N 7/012; H04N 9/045; H04N 2005/2255; A61B 1/0009; A61B 1/045; A61B 1/05
USPC .......................................................... 348/71
See application file for complete search history.

(56) References Cited

U.S. PATENT DOCUMENTS

| | | | | |
|---|---|---|---|---|
| 5,532,742 | A | * | 7/1996 | Kusaka .............. H04N 5/23248 348/222.1 |
| 5,959,670 | A | * | 9/1999 | Tamura .................... G06T 3/40 348/229.1 |
| 2002/0140806 | A1 | | 10/2002 | Abe et al. |
| 2005/0099540 | A1 | | 5/2005 | Elliott et al. |
| 2008/0100700 | A1 | | 5/2008 | Tannai |
| 2008/0100701 | A1 | | 5/2008 | Tannai |
| 2008/0100702 | A1 | | 5/2008 | Tannai |
| 2008/0183981 | A1 | | 7/2008 | Tannai |
| 2009/0049455 | A1 | * | 2/2009 | Ito ......................... G06F 1/3203 719/315 |
| 2009/0231476 | A1 | * | 9/2009 | Hagihara .............. H04N 5/2252 348/294 |
| 2014/0187867 | A1 | | 7/2014 | Fukuda |

FOREIGN PATENT DOCUMENTS

| | | |
|---|---|---|
| JP | 1-280439 A | 11/1989 |
| JP | 2000-184295 A | 6/2000 |
| JP | 2000-184295 A | 6/2000 |

OTHER PUBLICATIONS

Jan. 23, 2018 Japanese Office Action in counterpart Japanese Application No. 2014-155077.

* cited by examiner

ELECTRONIC ENDOSCOPE

BACKGROUND OF THE INVENTION

1. Field of the Invention

This invention relates to an endoscope system that is equipped with a video-scope and a video-processor, and particularly to enlarging an image that is obtained by the image sensor.

2. Description of the Related Art

A video-scope (electronic endoscope) is equipped with an image sensor. Since the size of the image sensor is restricted because of the thinness of the tip portion, the number of pixels in the image sensor is generally smaller than that of a monitor that displays an observed image. Therefore, an interpolation process is carried out to enlarge the size of an image obtained by the image sensor. Usually, one field's or frame's worth of image data is temporarily stored in a field/frame memory, and an interpolation process is carried out for the stored image data. However, an interpolation process with a field/frame memory increases electric power consumption and the amount of data to be transferred and processed, thereby decreasing a performance of a system.

To avoid reduced performance, an interpolation process that utilizes line memories is carried out. JP1989-261086A discloses the lower-order (e.g., the second order) interpolation process, in which an interpolation line is added by using two neighboring lines' worth of pixel data that are stored in line memories. JP2000-184295A discloses the simple interpolation process that adds an interpolation line by using a neighboring line directly.

The lower-order interpolation process or simple interpolation process using a line memory(s) cannot generate an enlarged image with high resolution. Recently, displaying an observed image with high quality is required to accurately diagnose certain medical problems. The above interpolation processes cannot sufficiently achieve the high quality required of an observed image in the endoscope field.

SUMMARY OF THE INVENTION

This invention is directed to provide an endoscope system that generates an enlarged image with high quality while using only a few line memory units.

An electronic endoscope with an image sensor, according to the present invention, has an image sensor driver configured to drive the image sensor to read one line's worth of image-pixel signals in order; at least four line memory units each configured to store one line's worth of image-pixel signals, respectively; and an interpolation processor that interpolates image-pixel signals of interpolated scanning lines to generate an enlarged image. The interpolation processor generates one line's worth of interpolated image-pixel signals based on image-pixel signals that are stored in the line memories. For example, the number of line memories is equal to the number of scanning lines that are used for an interpolation process. The image sensor is, for example, a charge transfer-type image sensor. In this case, the image sensor driver suspends an output of a vertical-transfer pulse signal.

In the present invention, the image sensor driver reads one line's worth of image-pixel signals intermittently, and the interpolation processor suspends the writing of image-pixel signals that are stored in the line memories in accordance to a suspension of the output of the one line's worth of image-pixel signals from the image sensor. The interpolation processor may generate one line's worth of interpolated image-pixel signals based on image-pixel signals that are stored in one of the line memories and one newly input line's worth of image-pixel signals. The interpolation processor may use one line's worth of image pixel signals that is stored directly in one of the three line memories when suspending the writing of the image-pixel signals.

For example, the interpolation processor shifts, in order, one line's worth of image-pixel signals stored in each line memory to a next line memory. A mask signal generator that outputs a mask signal to the image sensor driver at predetermined time interval may be included in the endoscope system. The image sensor driver may suspend reading of one line's worth of image-pixel signals when receiving the mask signal.

BRIEF DESCRIPTION OF THE DRAWINGS

Hereinafter, the preferred embodiment of the present invention is described with reference to the attached drawings.

DESCRIPTION OF THE PREFERRED EMBODIMENTS

Hereinafter, the preferred embodiment of the present invention is described with reference to the attached drawings.

Figure 1:
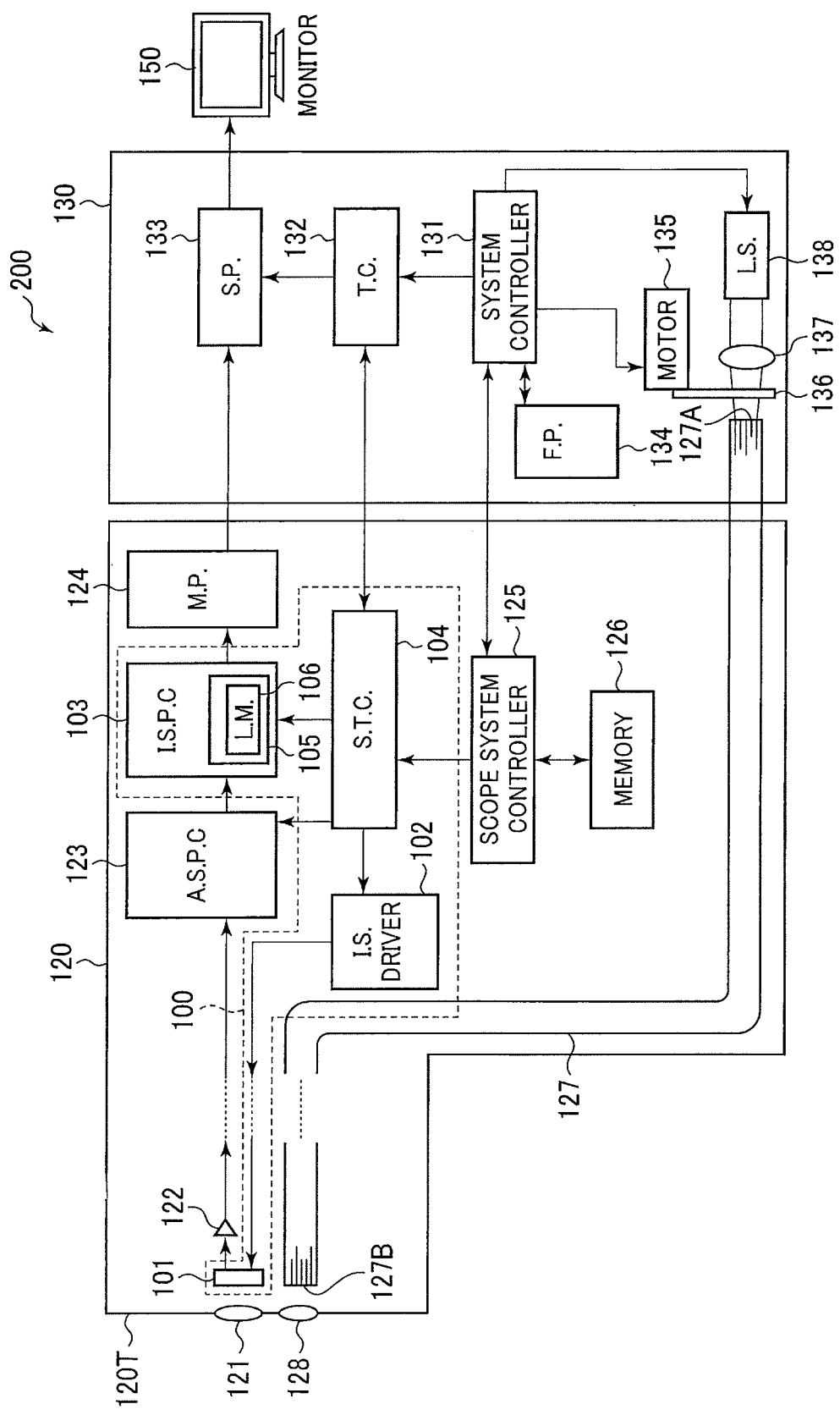
FIG. 1 is a block diagram of an endoscope system according to the present embodiment.
Figure 2:
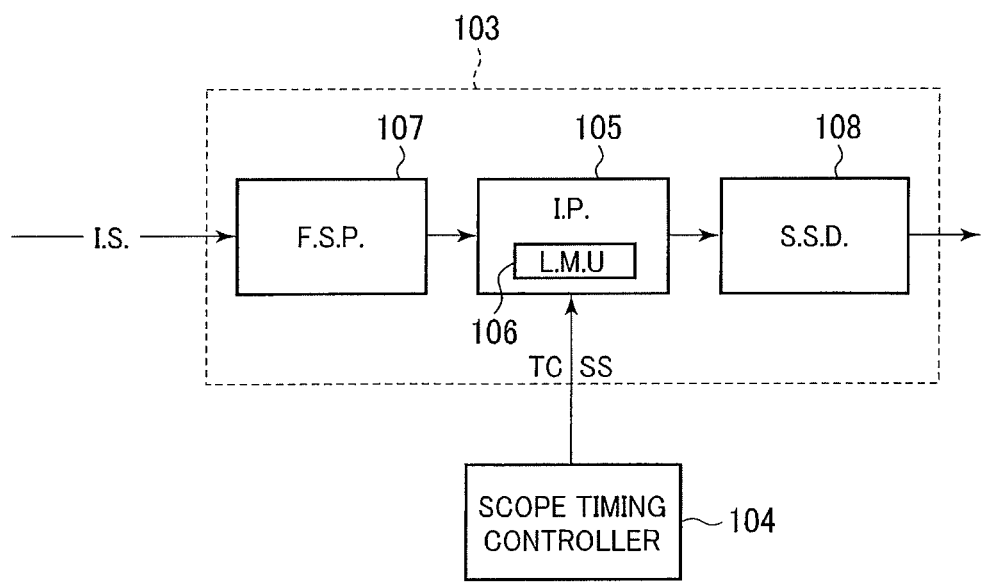
FIG. 2 is a block diagram of an image-signal processing circuit.

FIG. 1 is a block diagram of an endoscope system according to the present embodiment. FIG. 2 is a block diagram of an image-signal processing circuit.

The endoscope system is equipped with a video-scope (electronic endoscope) 120, which has an image sensor 101 in its tip portion, and a video-processor 130. The video-scope 120 is detachably connected to the video-processor 130, and a monitor 150 is connected to the video-processor 130. A light source 138 in the video-processor 130 emits illumination light toward the incident surface of a light guide 127. The light guide 127 that is provided in the video-scope 120 directs incident light to the tip portion 120T of the video-scope 120. The light passing through the light guide 127 and exiting from the tip portion 127B of the light guide 127, exits from the tip portion 120T of the video scope 120 via a diffusion lens 128. Thus, a target object may be illuminated.

Light reflected off the target object enters into a photographing optical system 121 and light passing through the photographing optical system 121 reaches a charge-transfer type image sensor 101 to form an object image on a photo-sensitive area of the image sensor 101. The image sensor 101 is herein a CCD and has a layout of an interline-transfer CCD, in which a plurality of photodiodes are arranged in a matrix, and a plurality of vertical transfer registers are arranged next to the photodiodes along the row direction, respectively. Charges that are accumulated in the photodiodes are transferred to the vertical-transfer registers simultaneously and transferred to the horizontal-transfer registers line by line. Then, one line's worth of accumulated charges, i.e., image-pixel signals, are transferred to the horizontal-transfer registers and output from the image sensor 101, in order. One field's or frame's worth of image-pixel signals are read out at predetermined time intervals (e.g., 1/60 or 1/50 seconds). An image sensor driver 102 outputs pulse signals to drive the image sensor 101. On the light-receiving surface of the image sensor 14, a color filter array is disposed.

Image-pixel signals that are read from the image sensor 101 line by line are amplified on an amplifier 122. The amplified image-pixel signals are digitalized on an analog signal processing circuit (A.S.P.C.) 123 and fed to an image-signal processing circuit (I.S.P.C.) 103. As shown in FIG. 2, The I.S.P.C 103 has a first signal processor 107, an interpolation processor 105, and a second signal processor 108. The digitized image-pixel signals (pixel data) are subjected to a given process on the first signal processor 107 and fed to the interpolation processor 105. The interpolation processor 105 has a line memory unit 106 and enlarges an image observed on one field/frame's worth of observed image in accordance to a user's operation. For example, when a user sets an enlargement process mode by operating an input device (not shown) connected to the video-processor 130, an enlarged image is displayed on the monitor 150.

As described below, the interpolation processor 105 interpolates a scanning line by using neighboring scanning lines to generate an enlarged image. An imaging processor 100 carries out an interpolation process substantially. In the second signal processor 108, image-pixel signals are subjected to a white balance process, color conversion process, and so on. Thus, color image data is generated. A masking processor 108 shown in FIG. 1 carries out a masking process on the edge portions of the generated image data. A signal processor 133 provided in the video-processor 130 processes color image data, in accordance with a video standard, and outputs the image data to the monitor 150. Thus, an observed image is displayed on the monitor 150 in real time.

A scope system controller 125 in the video-scope 120 controls the scope timing controller (S.T.C.) 104. The scope timing controller 104 outputs timing signals (clock pulse signals) to the analog-signal processing circuit 123, the image signal processing circuit 103, and the image sensor driver 102. Also, the scope system controller 125 reads data associated with characteristics of the video-scope 10 from a memory 126. The image sensor driver 102 sends various pulse signals to the image sensor 101 while synchronizing with timing signals fed from the scope timing controller 104. Concretely, the image sensor driver 102 outputs vertical-reading pulse signals, vertical-transfer pulse signals, and horizontal-transfer pulse signals. Respective pulse signals are fed to the image sensor 101 periodically. In this way, an imaging apparatus 100 that includes the image sensor 101, the image-signal processing circuit 103, the scope timing controller 104, and the image sensor driver 102 generates an enlarged image.

A system controller 131 in the video-processor 130 controls the motion of the video-processor 130 by outputting control signals to a timing controller 132, the light source 138, etc. The timing controller 132 outputs clock pulses to the signal processor 133 and the scope timing controller 104. Also, the system controller 131 communicates with the scope system controller 125. Switch buttons (not shown) provided on the front panel 134 are operated by a user. A stop or diaphragm 136 is opened and closed by a motor 135 to adjust the brightness of an observed image displayed on the monitor 150.

Figure 3:
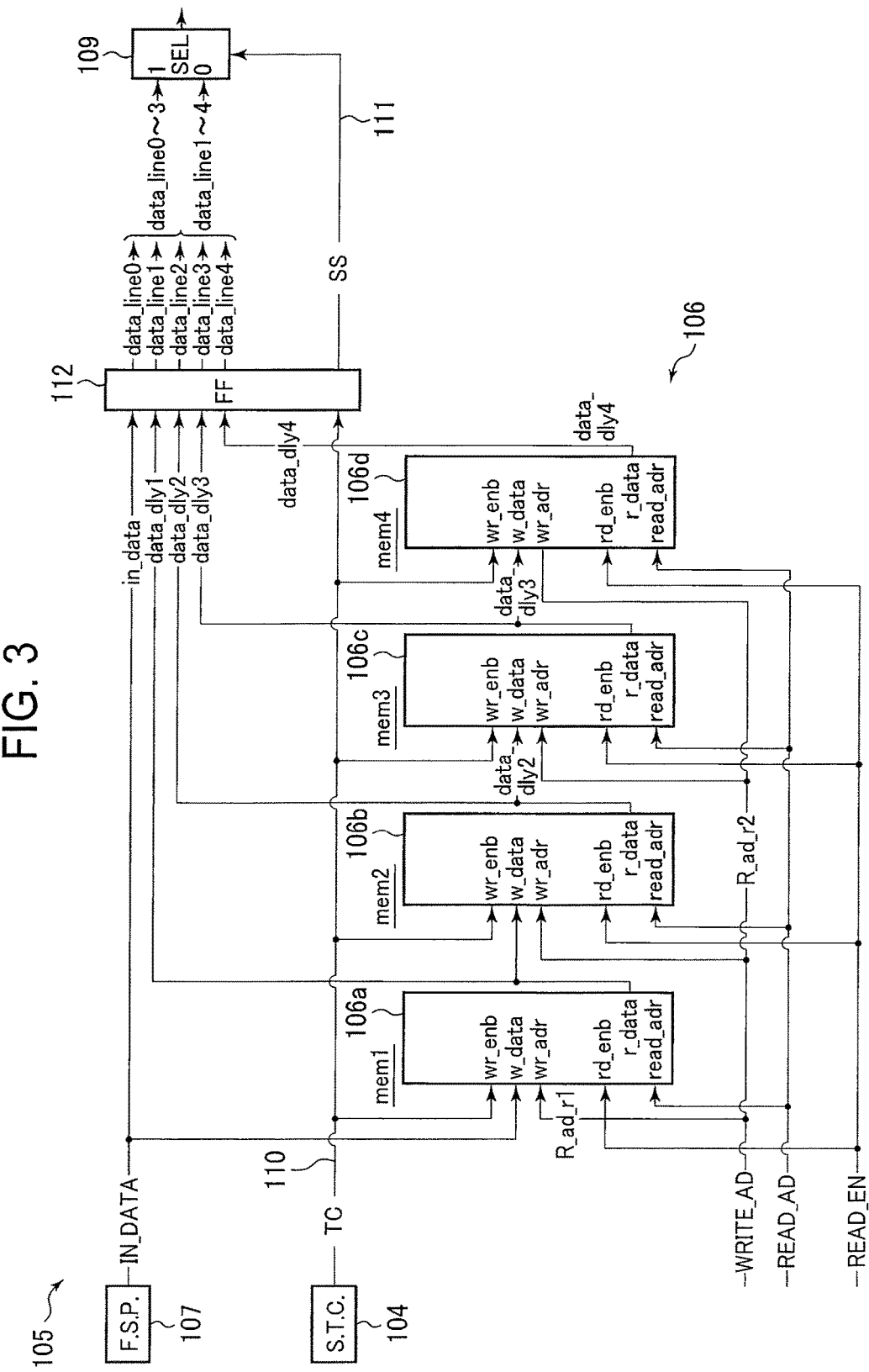
FIG. 3 is a block diagram of the interpolation processor 105.

FIG. 3 is a block diagram of the interpolation processor 105.

The interpolation processor 105 has a selector 109, and a flip-flop circuit 112, in addition to the line memory unit 106. The line memory unit 106 has a first line memory 106a, a second line memory 106b, a third line memory 106c, and a fourth line memory 106d, which are connected to a signal line 110, respectively. The signal line 110 is connected to the scope timing controller 104 and transmits a control signal TC that suspends the writing of data. Each line memory does not rewrite data, instead maintaining present data when receiving the control signal TC.

The first, second, third, and fourth line memories 106a-106d store and output one line's worth of image-pixel signals (hereinafter, called "pixel data") to the flip flop 112, respectively. The selector 109 is connected to the scope timing controller 104 and selectively outputs four lines' worth of pixel data in accordance to a selection signal (SS) that is fed from the scope timing controller 104. Concretely, the selector 109 selects a first combination of one line's worth of pixel data, which are output from the first signal processor 107, and three lines' worth of pixel data that are read out from the first, second, and third line memories 106a-106c, or a second combination of the four lines' worth of pixel data that are read out from the first to fourth line memories 106a-106d. The interpolation processor 105 generates an enlarged image on the basis of the first or second combination.

Figure 4:
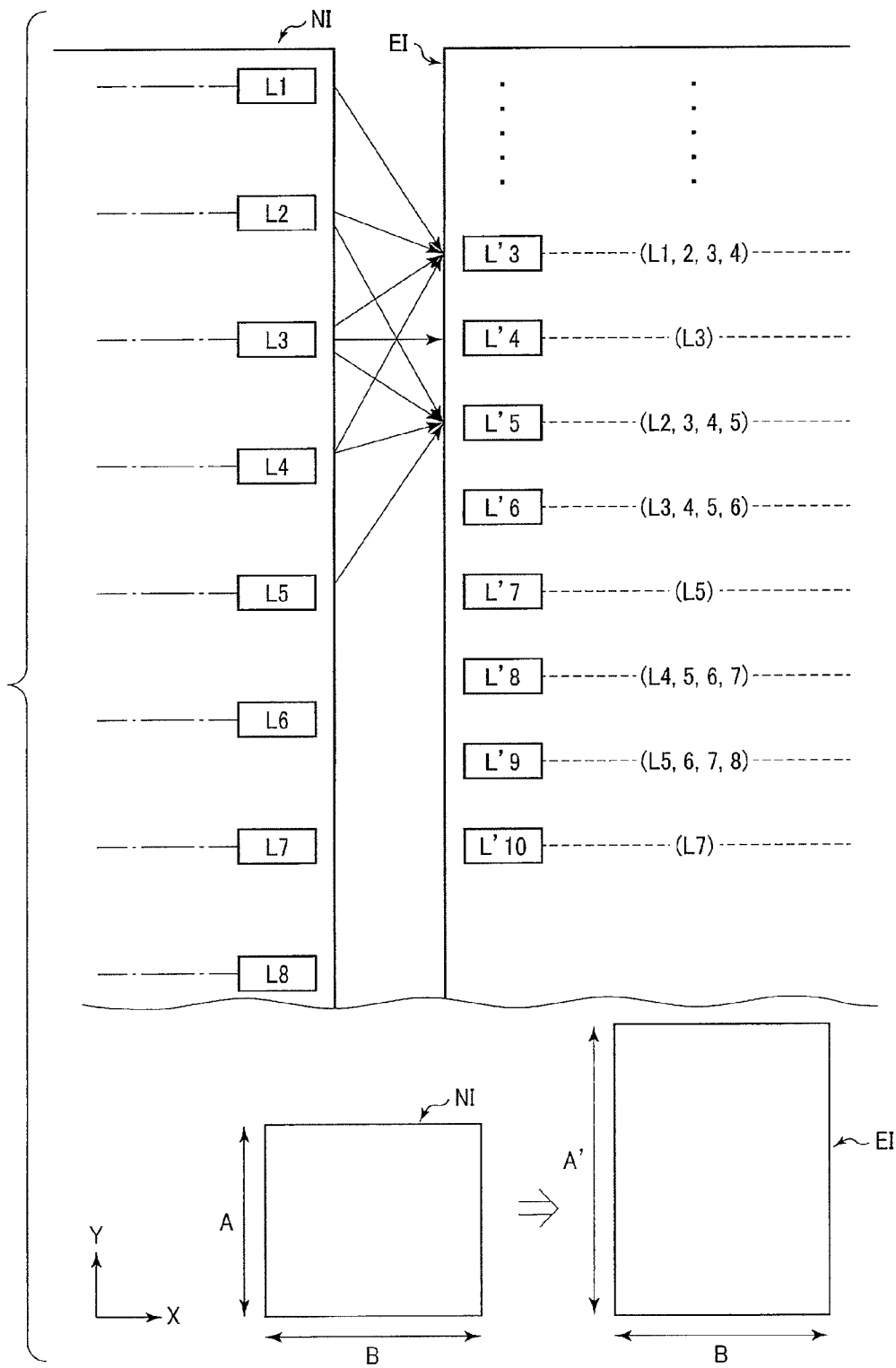
FIG. 4 is a view showing a normal image and an enlarged image.
Figure 5:
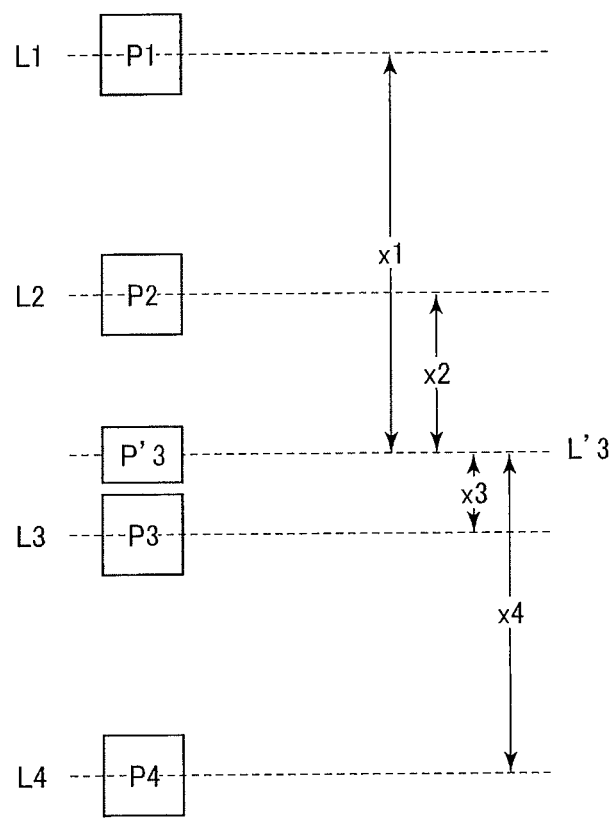
FIG. 5 is an interpolation process based on the bicubic method.

Hereinafter, an interpolation process is explained with reference to FIGS. 4 and 5. FIG. 4 is a view showing a normal image and an enlarged image. FIG. 5 is an interpolation process based on the bicubic method.

In FIG. 4, a normal image NI and an enlarged image EI are shown. The interpolation process herein interpolates pixels along a vertical direction such that the number of scanning lines along the vertical direction "A" in the normal image NI is changed to the number "A'". On the other hand, the number of lines along the horizontal direction "B" does not change. The magnification factor (=A'/A) along the vertical direction is herein set to 1.5. A scanning line is regularly and periodically interpolated when enlarging the normal image NI. In the case of the magnification factor "1.5", one scanning line is interpolated relative to two scanning lines. Then, one line's worth of pixel data to be arrayed in an interpolated scanning line is generated from pixel data arrayed in neighboring scanning lines. Herein, based on the bicubic interpolation, four neighboring scanning lines are used to interpolate an interpolated scanning line. For example, as shown in FIG. 5, an interpolated scanning line L'3 in the enlarged image EI is obtained from neighboring scanning lines L1, L2, L3, and L4 in the normal image NI. Concretely speaking, a given interpolated pixel data P'3 are obtained from pixel data "P1", "P2", "P3", and "P4". Note that the X coordinates of the pixels "P1", "P2", "P3", and "P4" are the same as those of the interpolated pixel "P'3".

Generally, any given pixel data in an interpolated scanning line can be obtained by the following formula:

$$P' = W_{n-1}P_{n-1} + W_n P_n + W_{n+1}P_{n+1} + W_{n+2}P_{n+2} (n>2) \quad (1)$$

Note that "P'" represents an interpolated pixel and "$P_{n-1}$", "$P_n$", "$P_{n+1}$", and "$P_{n+2}$" represent pixels arrayed in four neighboring scanning lines "$L_{n-1}$", "$L_n$", "$L_{n+1}$", and "$L_{n+2}$". Note that the X coordinates of the pixels "$P_{n-1}$", "$P_n$", "$P_{n+1}$", and "$P_{n+2}$" are the same as that of the interpolated pixel "P".

The weighting coefficient represented by "$W_n$" is obtained by the following formula. Note that "$x_n$" represents a distance between a scanning line, which has a corresponding pixel and an interpolated scanning line (See FIG. 5). Also, "a" is a constant value (e.g., a=−1).

$$W_n=(a+2)|x_n^3|-(a+3)|x_n^2|+1 \ (|x_n|\le 1.0)$$

$$W_n=a|x_n^3|-5ax_n2+8a|x_n|-4 \ (1.0\le |x_n|<2)$$

$$W_n=0 \ (2.0\le |x_n|) \quad (2)$$

The other weighting coefficients "$W_{n-1}$", "$W_{n+1}$", and "$W_{n+2}$" are also obtained by the above formula (2).

The above formula (1) is utilized when interpolating a scanning line. On the other hand, a scanning line in the normal image NI is directly used as a scanning line in the enlarged image EI. For example, scanning lines L3, L5, and L7 becomes scanning line L'4, L'7, and L'10, respectively (see FIG. 4).

Figure 6:
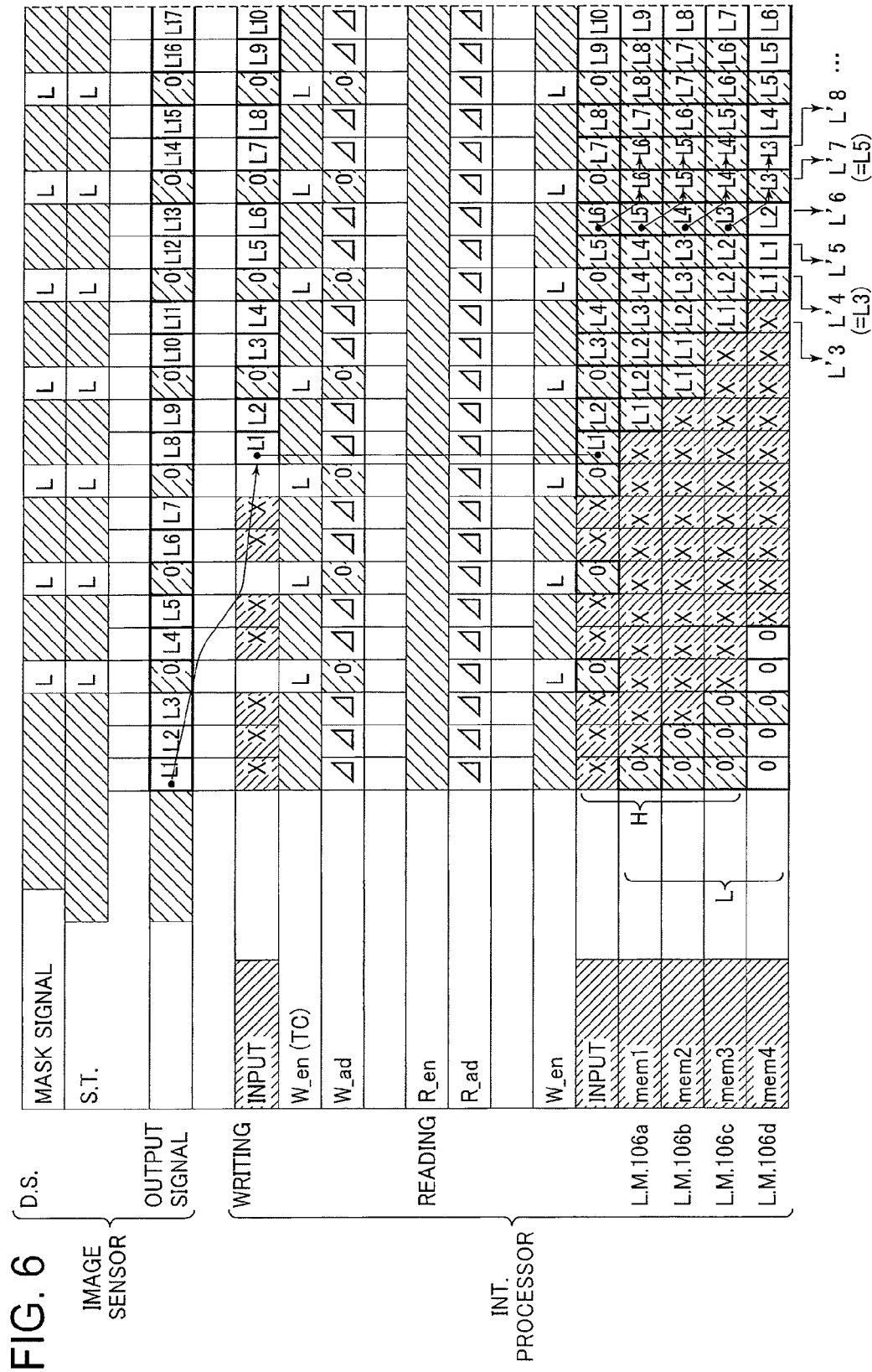
FIG. 6 is a timing chart showing the driving process for the image sensor and the reading/writing process of the line memory unit.

FIG. 6 is a timing chart showing the driving process for the image sensor 101 and the reading/writing process of the line memory unit 106.

The output timing of image-pixel signals from the image sensor 101 and the output timing of generated interpolated image-pixel signals are synchronized with one another in accordance to the video standard. On the other hand, since the number of scanning lines "A'" in the enlarged image EI is larger than the number of scanning lines "A" in the normal image NI and the interpolation process requires a given amount of processing time, the successive reading of one line's worth of image-pixel signals from the image sensor 101 does not allow the interpolation process to generate interpolated scanning lines successively. This is because one line's worth of pixel data stored in a line memory is rewritten one after another so that one line's worth of pixel data that are needed for using the above formula (1) have been erased from the line memory. To secure the amount of time that is needed for an interpolation process, the image sensor 101 outputs one line's worth of image-pixel signals intermittently. Herein, the outputting of one line's worth of image-pixel signals is suspended once every three times. Concretely, the scope timing controller 104 outputs a mask signal to the image sensor driver 102 after every reading of two lines' worth of image-pixel signals, as shown in FIG. 6. The image sensor driver 102 outputs a "Low" signal in response to the mask signal so that one line's worth of charges stored in the vertical-transfer register are not transferred to the horizontal-transfer register and one line's worth of image-pixel signals that output from the image sensor 101 consequently become signals having the value of "zero". In FIG. 6, one line's of worth of image-pixel signals output from the image sensor 101 are designated as "L1, L2, L3, 0 (zero), L4, L5, 0, L6, L7, 0, L8, L9, . . . ". Note that, since one line's worth of image-pixel signals are input to the interpolation processor 105 via the amplifier 122, the analog signal processing circuit 123, and the first processor 107, a given time passes when one line's worth of pixel data are input to the interpolation processor 105 (See FIG. 6).

As described above, each of the line memories 106a to 106d stores one line's worth of pixel data and shifts stored pixel data to the next line memory in accordance to clock pulse signals. The image memory 106a first receives an input of one line's worth of pixel data and then the image memory 106d receives the data afterward. On the other hand, when pixel data "zero" is input to the interpolation processor 105, the interpolation processor 105 outputs a writing control signal (Low signal) that prohibits the writing of pixel data to the image memories 106a to 106d. Thus, the pixel data stored in image memories 106a to 106d are not rewritten during the next processing interval.

When one line's worth of pixel data (not zero) are input to the interpolation processor 105, the interpolation processor 105 uses three lines' worth of pixel data, which are stored in the line memories 106a, 106b, and 106c, and one line's worth of pixel data that is input currently to carryout an interpolation process. For example, the interpolated scanning line L'3 is generated based on pixel data of the scanning lines L1, L2, L3, which are stored in the line memories 106a, 106b, and 106c, and pixel data of the scanning line L4 that is input to the interpolation processor 105. On the other hand, when zero data is input to the interpolation processor 105, the interpolation processor 105 uses the four lines' worth of pixel data that is stored in the line memories 106a, 106b, 106c, and 160d to carry out the interpolation process. Actually, only one line's worth of pixel data that are stored in one of the line memories 106a to 106d is utilized directly. For example, the interpolated scanning line L'4 is generated by using the scanning line L3 directly.

Such an intermittent output of one line's worth of pixel-image signals and an intermittent writing of pixel data satisfies the three-order interpolation process based on the bicubic method, which is a rapid interpolation process. Especially, the interpolation process can be carried out by only the four line memories 106a to 106d. Thus, a high-quality enlarged image with high quality can be displayed on the monitor 150 without a delay. Especially, the number of line memories can be set to a few numbers.

An interpolation process along the horizontal direction may be performed by using the bicubic method. Also, the magnification factor may be set to an arbitrary value. A higher-order interpolation process may be carried out. In this case, the number of line memories is set to correspond to the number of scanning lines that are used for the interpolation process. Another type image sensor other than the CCD may be applied.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2014-155077 (filed on Jul. 30, 2014), which is expressly incorporated herein by reference, in its entirely.

The invention claimed is:

1. An electronic endoscope with an image sensor, comprising:
an image sensor driver configured to drive said image sensor to read one line's worth of image-pixel signals in order;
at least four line memories configured to store one line's worth of image-pixel signals, respectively, wherein a number of line memories "N" of the at least four line memories is equal to a number of lines that are used for an interpolation process; and
an interpolation processor that interpolates image-pixel signals of interpolated scanning lines to generate an enlarged image, wherein:

said interpolation processor shifts one line's worth of image pixel signals stored in each line memory to a next line memory, in order;

said interpolation processor generates one line's worth of interpolated image-pixel signals on the basis of "N−1" line's worth of image-pixel signals that are stored in "N−1" line memories, and newly inputs one line's worth of image-pixel signals when reading one line's worth of image pixel signals; and said interpolation processor generates one line's worth of interpolated image-pixel signals on the basis of "N" line's worth of image pixel signals that are stored in the line memories when suspending the reading of one line's worth of image pixel signals from the image sensor, said image sensor driver reads one line's worth of image-pixel signals intermittently, and said interpolation processor suspends a shifting of one line's worth of image-pixel signals during a next processing interval, when one line's worth of image-pixel signals are not input to said interpolation processor.

2. The endoscope of claim 1, wherein said interpolation processor directly uses one line's worth of image pixel signals that are stored in one of a three line memories when suspending the writing of the image-pixel signals.

3. The endoscope of claim 1, further comprising a mask signal generator that outputs a mask signal to said image sensor driver at a predetermined time interval, said image sensor driver suspending reading of one line's worth of image-pixel signals when receiving the mask signal.

4. The endoscope of claim 1, wherein said image sensor comprises a charge transfer-type image sensor, said image sensor driver suspending an output of a vertical-transfer pulse signal.

* * * * *